United States Patent
Kang et al.

(10) Patent No.: US 12,053,574 B2
(45) Date of Patent: Aug. 6, 2024

(54) DRY POWDER INHALER WITH DRUG INLET MESH NETWORK

(71) Applicant: KOREA UNITED PHARM. INC., Sejong (KR)

(72) Inventors: Won Ho Kang, Seoul (KR); Youn Woong Choi, Ansan (KR); Dae Chul Ha, Sejong (KR); Seung Jin Yang, Daejeon (KR); Gweon Hee Yu, Gwangju (KR); Kyu Yeol Nam, Anyang (KR); Kyu Chul Jang, Seoul (KR)

(*) Notice: Subject to any disclaimer, the term of this patent is extended or adjusted under 35 U.S.C. 154(b) by 1193 days.

(21) Appl. No.: 16/626,410

(22) PCT Filed: Jun. 29, 2017

(86) PCT No.: PCT/KR2017/006901
§ 371 (c)(1),
(2) Date: Dec. 24, 2019

(87) PCT Pub. No.: WO2019/004501
PCT Pub. Date: Jan. 3, 2019

(65) Prior Publication Data
US 2020/0139057 A1    May 7, 2020

(30) Foreign Application Priority Data
Jun. 27, 2017  (KR) .................... 10-2017-0081320

(51) Int. Cl.
*A61M 15/00* (2006.01)
*A61K 9/00* (2006.01)
(Continued)

(52) U.S. Cl.
CPC ....... *A61M 15/0005* (2014.02); *A61K 9/0075* (2013.01); *A61K 47/26* (2013.01); *A61K 47/36* (2013.01)

(58) Field of Classification Search
CPC .................. A61M 15/0005; A61M 11/003
See application file for complete search history.

(56) References Cited

U.S. PATENT DOCUMENTS 2,517,482 A * 8/1950 Hall ................. A61M 15/0028
                                                128/203.15
2,569,720 A * 10/1951 Jesnig ............... A61M 15/0031
                                                128/203.15
(Continued)

FOREIGN PATENT DOCUMENTS

DE   102007058112 A1 * 6/2009 .......... A61M 15/001
GB        726916 A  *  3/1955
(Continued)

OTHER PUBLICATIONS

Notice of Reasons for Refusal for JP 2019-572757 mailed on Feb. 2, 2021.
(Continued)

*Primary Examiner* — Kathryn E Ditmer (57) ABSTRACT

The present invention relates to a dry powder inhaler. The dry powder inhaler includes an inhaler housing, a drug container configured to be provided in the inhaler housing and accommodate the dry powder drug, a drug inlet configured to be disposed above the drug container and through which the dry powder drug is inhaled, and a mesh network configured to be installed on a path of the drug inlet and have a mesh part for collision with the dry powder drug formed therein.

13 Claims, 7 Drawing Sheets

(51) Int. Cl.
*A61K 47/26* (2006.01)
*A61K 47/36* (2006.01)

(56) References Cited

U.S. PATENT DOCUMENTS

| | | | | |
|---|---|---|---|---|
| 3,807,400 | A * | 4/1974 | Cocozza | A61M 15/0033 |
| | | | | 128/203.15 |
| 4,013,075 | A * | 3/1977 | Cocozza | A61M 15/0028 |
| | | | | 222/85 |
| 5,724,959 | A * | 3/1998 | McAughey | A61M 15/00 |
| | | | | 128/203.15 |
| 5,787,881 | A * | 8/1998 | Chawla | A61M 15/0028 |
| | | | | 128/203.15 |
| 5,829,434 | A | 11/1998 | Ambrosio et al. | |
| 6,098,619 | A * | 8/2000 | Britto | A61M 15/0028 |
| | | | | 128/203.15 |
| 6,245,339 | B1 * | 6/2001 | Van Oort | A61M 15/0048 |
| | | | | 128/203.19 |
| 6,418,926 | B1 * | 7/2002 | Chawla | A61M 11/003 |
| | | | | 128/203.15 |
| 6,705,313 | B2 * | 3/2004 | Niccolai | A61M 15/0008 |
| | | | | 128/203.15 |
| 8,365,725 | B2 | 2/2013 | King et al. | |
| 8,651,104 | B2 | 2/2014 | Donovan et al. | |
| 9,125,998 | B2 * | 9/2015 | Harmer | A61M 15/0021 |
| 2003/0000523 | A1 * | 1/2003 | Citterio | A61M 15/0028 |
| | | | | 128/203.15 |
| 2003/0015195 | A1 | 1/2003 | Haaije de Boer et al. | |
| 2005/0039744 | A1 | 2/2005 | Szirmai | |
| 2006/0278086 | A1 * | 12/2006 | Inagaki | B01D 46/0028 |
| | | | | 96/223 |
| 2007/0125375 | A1 | 6/2007 | Finlay et al. | |
| 2007/0151562 | A1 * | 7/2007 | Jones | A61M 15/0005 |
| | | | | 128/203.15 |
| 2008/0127971 | A1 | 6/2008 | King et al. | |
| 2008/0163871 | A1 * | 7/2008 | Bozoky | A61M 15/02 |
| | | | | 239/8 |
| 2011/0094507 | A1 * | 4/2011 | Wachtel | A61M 15/0051 |
| | | | | 128/200.21 |
| 2012/0291780 | A1 | 11/2012 | Donovan et al. | |
| 2014/0048065 | A1 * | 2/2014 | Haroutunian | F15D 1/001 |
| | | | | 128/203.15 |
| 2015/0107589 | A1 * | 4/2015 | Longest | A61K 47/12 |
| | | | | 128/203.15 |
| 2015/0283338 | A1 * | 10/2015 | Colosio | A61M 15/0028 |
| | | | | 128/203.15 |
| 2017/0333646 | A1 * | 11/2017 | Hemy | A61M 15/0005 |
| 2020/0030554 | A1 * | 1/2020 | Zarogoulidis | A61M 11/003 |

FOREIGN PATENT DOCUMENTS

| | | |
|---|---|---|
| JP | 2000-503565 A | 3/2000 |
| JP | 2000-515787 A | 11/2000 |
| JP | 2002-513649 A | 5/2002 |
| JP | 2006-507876 A | 3/2006 |
| KR | 10-2010-0134700 A | 12/2010 |
| KR | 10-2014-0093353 A | 7/2014 |
| WO | WO-2018033793 A1 * | 2/2018 ......... A41D 13/1192 |

OTHER PUBLICATIONS

Japanese Office Action for JP Patent Application 2019-572757 dated Sep. 28, 2021.
International Search Report for PCT/KR2017/006901 mailed on Feb. 23, 2018.

* cited by examiner

| 250 | KUPD#1 | | | | | | | |
|---|---|---|---|---|---|---|---|---|
| | AREA | | Effective amount (μg) | | Effective amount (%) | | | |
| | salmeterol | fluticasone | salmeterol | fluticasone | salmeterol | fluticasone | salmeterol | fluticasone |
| M | 71897 | 577771 | 2.10 | 9.51 | 4.20% | 3.80% | 4.20% | 3.80% |
| I | 117578 | 1151234 | 3.43 | 18.95 | 6.87% | 7.58% | 6.87% | 7.58% |
| stage 1 | 691837 | 6224873 | 20.20 | 102.47 | 40.39% | 40.99% | 45.67% | 46.36% |
| stage 2 | 90273 | 815441 | 2.64 | 13.42 | 5.27% | 5.37% | | |
| stage 3 | 117823 | 1226038 | 3.44 | 20.18 | 6.87% | 8.07% | 21.39% | 24.67% |
| stage 4 | 165217 | 1695788 | 4.82 | 27.91 | 9.65% | 11.17% | | |
| stage 5 | 83433 | 824962 | 2.44 | 13.58 | 4.87% | 5.43% | | |
| stage 6 | 38633 | 194351 | 1.13 | 3.20 | 2.26% | 1.28% | 4.19% | 1.97% |
| stage 7 | 10347 | 59792 | 0.30 | 0.98 | 0.60% | 0.39% | | |
| MOC | 22780 | 46082 | 0.67 | 0.74 | 1.33% | 0.30% | | |
| Total value | 528303 | 4861414 | 41.16 | 210.95 | 82.32% | 84.38% | 82.32% | 84.38% |

FIG. 11

| 250 | KUPD#2 | | | | | | | |
|---|---|---|---|---|---|---|---|---|
| | AREA | | Effective amount (μg) | | Effective amount (%) | | | |
| | salmeterol | fluticasone | salmeterol | fluticasone | salmeterol | fluticasone | salmeterol | fluticasone |
| M | 84090 | 728826 | 2.46 | 12.00 | 4.91% | 4.80% | 4.91% | 4.80% |
| I | 108562 | 1058495 | 3.17 | 17.42 | 6.34% | 6.97% | 6.34% | 6.97% |
| stage 1 | 629977 | 5553482 | 18.40 | 91.41 | 36.79% | 36.57% | 41.90% | 42.18% |
| stage 2 | 87368 | 853011 | 2.55 | 14.04 | 5.10% | 5.62% | | |
| stage 3 | 131002 | 1376668 | 3.83 | 22.66 | 7.65% | 9.06% | 22.42% | 27.10% |
| stage 4 | 172243 | 1868641 | 5.03 | 30.76 | 10.06% | 12.30% | | |
| stage 5 | 80714 | 870126 | 2.36 | 14.32 | 4.71% | 5.73% | | |
| stage 6 | 15812 | 164044 | 0.46 | 2.70 | 0.92% | 1.08% | 3.33% | 2.09% |
| stage 7 | 37471 | 103384 | 1.09 | 1.70 | 2.19% | 0.68% | | |
| MOC | 3729 | 50536 | 0.11 | 0.83 | 0.22% | 0.33% | | |
| Total value | 528359 | 5286500 | 39.46 | 207.86 | 78.90% | 83.14% | 78.90% | 83.14% |

DRY POWDER INHALER WITH DRUG INLET MESH NETWORK

CROSS REFERENCE TO RELATED APPLICATIONS

This application claims priority to Korean Patent Application No. 10-2017-0081320, filed on Jun. 27, 2019. Further, the application is the National Phase application of International Application No. PCT/KR2017/006901, filed on Jun. 29, 2019, which designates the United States. Each of these applications is hereby incorporated by reference in their entirety into the present application.

TECHNICAL FIELD

The present invention relates to a dry powder inhaler, and more particularly to a dry powder inhaler for delivering a drug of dry powder inhalation formulation to lungs.

BACKGROUND ART

Inhalation formulations have been used for the treatment of respiratory diseases such as asthma and chronic obstructive pulmonary disease (COPD), and inhalation formulations of drugs for the treatment of lung cancer, diabetes, and degenerative brain diseases have also been studied.

Inhalants have the advantage of achieving the desired therapeutic effect with a small amount of the active ingredient, whereas only a fraction of the active ingredient administered reaches the target site, and the active ingredient reaches other organs that do not require treatment, causing side effects.

Therefore, there is a medical unmet need for maximizing drug efficacy by allowing the active ingredient to be repeatedly targeted to the target site and preventing the active ingredient from reaching an organ that does not require treatment.

Inhalers in which drugs are inhaled with air to be administered to the respiratory tract for effective administration of inhalants are widely used for the treatment of respiratory diseases. Typically, the metered dose inhaler (MDI) has been widely used to preoccupy 80% of the inhaler market since it was first approved in 1956, but as environmental issues such as ozone depletion and global warming have emerged, recently, research on dry powder inhaler (DPI) has begun. Currently, DPI formulations are at a stage to compensate for the disadvantages of MDI formulations. MDI has the disadvantage that stability is reduced because the solvent and pharmacologically active ingredient, which can be used as a propellant, are compressed, and the spraying speed is fast so that the pharmacologically active ingredient reaches the throat too quickly, while DPI is easy to use and consists only of solid powder particles, which has the advantage of better stability.

In the case of such a DPI, the effective amount of the inhalant delivered to the lungs may vary according to the structure in the inhaler in the process of inhaling the inhalant, and there is a need for the development of an inhaler that can maximize the effective amount.

DISCLOSURE

Technical Problems

The present invention provides a dry powder inhaler having a structure capable of maximizing the effective amount of a drug of dry powder inhalation formulation to lungs.

Technical Solutions

According to an embodiment of the present invention, a dry powder inhaler according to the present invention may include an inhaler housing, a drug container configured to be provided in the inhaler housing and accommodate the dry powder drug, a drug inlet configured to be disposed above the drug container and through which the dry powder drug is inhaled, and a mesh network configured to be installed on a path of the drug inlet and have a mesh part for collision with the dry powder drug formed therein.

At least two mesh networks may be installed on the path of the drug inlet.

The mesh part may be alternately formed with respect to an inhaling direction of the dry powder drug.

The inhaler housing may include: an outer housing; and an inner housing accommodated in the outer housing, wherein the drug inlet may be formed over the outer housing and the inner housing, and a gap for air inflow is formed between the outer housing and the inner housing.

An inlet hole for air inflow from an outside may be formed at one side of the inhaler housing.

The mesh network may include: a first mesh network configured to be installed at an entrance of the drug inlet; and a second mesh network configured to be installed at an exit of the drug inlet.

A mesh network installed at a lowest end among the mesh networks may be disposed at a position spaced upwardly from an entrance of the drug inlet.

The mesh part may be formed more densely from a bottom to a top.

The mesh network may be made of a water-soluble material.

A water-soluble material may be coated on the surface of the mesh network.

The active ingredient may be one or more selected from the group consisting of Flutic as one, Salmeterol, Arformoterol, Budesonide, Fenotrol, Procaterol, Lev albuterol, Salbutamol, Albuterol, Terbutaline, Formoterol, Indacaterol, Olodaterol, Vilanterol, Ipratropium, Oxitropium, Aclidinium, Glycopyrronium, Tiotropium, Umeclidinium, Beclomethasone, Ciclesonide, Triamcinolone, Mometasone; Gefitinib, Erlotinib, Afatinib, Ossimtinib, Olmutinib, Crizotinib and Seritinib which are lung cancer targeted drugs; Levodopa which is used to treat Parkinson's disease; Quinolones, which is an antibiotic, and their pharmaceutically acceptable salts.

The active ingredient may be one or more selected from the group consisting of Insulin, Glucagon-Like Peptide (GLP), Glucose-dependent Insulinotropic Polypeptide (GIP), Human Growth Hormone (HGH), Parathyroid Hormone (PTH), Erythropoiesis-Stimulating Agents (ESA) and their analogs.

The active ingredient may have a particle size of 0.1 to 10.0 μm.

The carrier may be one or more selected from the group consisting of lactose, glucose, fructose, sucrose, maltose, raffinose, melezitose, mannitol, lactitol, maltitol, xylitol, dextrin and starch.

The carrier may have a particle size of 1 to 200 μm.

Advantageous Effects

According to an embodiment of the present invention, as an active ingredient and a carrier are separated from each other through the collision of a mesh network in which drugs of a formulation for dry powder inhalation including the active ingredient and the carrier are alternately formed, it is possible to maximize the effective amount by which the active ingredient, contained in the drugs of the formation for dry powder inhalation, is delivered to the lungs.

BRIEF DESCRIPTION OF THE DRAWINGS

FIG. 1 is a view showing the main portion of a dry powder inhaler according to an embodiment of the present invention.

FIG. 2 is a view showing an embodiment in which two mesh networks are arranged.

FIG. 3 is a view showing another embodiment in which two mesh networks are arranged.

FIG. 4 is a view showing an embodiment in which three mesh networks are arranged.

FIG. 5 is a view showing that a first mesh network is spaced upwardly from the inlet of a drug inlet.

FIG. 6 is a view showing a drug intake according to another embodiment of the present invention.

FIG. 7 is a graph showing the particle size distribution of fluticasone used as an active ingredient of a dry powder drug.

FIG. 8 is a graph showing the particle size distribution of salmeterol used as an active ingredient of the dry powder drug.

FIG. 9 shows the results of confirming the delivery amount of NGI to each stage using the seretide 250 as a reference drug.

FIG. 10 is a view showing a result of confirming the delivery amount of each NGI to each stage using KUPD #1.

FIG. 11 is a view showing a result of confirming the delivery amount of each NGI to each stage using KUPD #2.

DETAILED DESCRIPTION OF THE PREFERRED EMBODIMENTS

As the invention allows for various changes and numerous embodiments, particular embodiments will be illustrated in the drawings and described in detail in the written description. However, this is not intended to limit the present invention to the specific form disclosed, and it should be understood to include all changes, equivalents, and substitutes included in the spirit and scope of the present invention. In the following description of the present invention, if it is determined that the detailed description of the related known technology may obscure the gist of the present invention, the detailed description thereof will be omitted.

Terms such as "first" and "second" may be used to describe various components, but the components should not be limited by the terms. The terms are used only for the purpose of distinguishing one component from another.

The terminology used herein is for the purpose of describing particular examples only and is not intended to limit the scope of the present invention. Singular expressions include plural expressions unless the context clearly indicates otherwise. In this application, it should be understood that terms such as "include" or "have" are intended to indicate that there is a feature, number, step, operation, component, part, or a combination thereof described on the specification, and they do not exclude in advance the possibility of the presence or addition of one or more other features or numbers, steps, operations, components, parts or combinations thereof.

Hereinafter, an embodiment of a dry powder inhaler according to the present invention will be described in detail with reference to the accompanying drawings, and in the description with reference to the accompanying drawings, the same or corresponding components will be given the same reference numerals and redundant description thereof will be omitted. In addition, the dry powder inhaler described below is due to a dry powder drug supply mechanism of seretide, which is an inhaler used for asthma and chronic obstructive pulmonary disease, but is not necessarily limited thereto and can be used for various types of dry powder inhalers.

FIG. 1 is a view showing the main portion of a dry powder inhaler according to an embodiment of the present invention, FIG. 2 is a view showing an embodiment in which two mesh networks are arranged, and FIG. 4 is a view showing an embodiment in which three mesh networks are arranged.

According to the figures, the dry powder inhaler includes an inhaler housing 10, a drug container 62 configured to be provided in the inhaler housing 10 and accommodate the dry powder drug, a drug inlet 20 configured to be disposed above the drug container 62 and through which the dry powder drug is inhaled, and a mesh network 30, 40 or 50 configured to be installed on a path of the drug inlet 20 and have a mesh part 32, 42 or 52 for collision with the dry powder drug formed therein.

The inhaler housing 10 may accommodate a variety of devices that can be supplied with dry powder drugs therein. For example, the inside of the inhaler housing 10 may be provided with a drug supply unit supplied in the state in which the drug sheet 60 is wound, a sheet winding unit in which the drug sheet 60 is wound after the dry powder drug is inhaled, etc. For reference, reference numeral 2 is a cover coupled to the outer surface of the inhaler housing 10.

In the present embodiment, the inhaler housing 10 may include an outer housing 12 and an inner housing 14 installed inside the outer housing 12. The outer housing 12 may be made into a disk shape having an approximately predetermined thickness, and the inner housing 14 may be formed so as to partition a space occupied by the above-described drug supply unit, the sheet winding unit, and the like. Since the inner housing 14 is installed inside the outer housing 12, it is possible to minimize the uninhaled drug from being attached or moved in the outer housing 12 after the dry powder drug is supplied from the inner housing 14. Further, one side of the outer housing 12 is provided with a mouthpiece 16 where a patient directly contacts the mouth.

On the other hand, the inhaler housing 10 is provided with a drug inlet 20 which is a passage through which the dry powder drug is inhaled. The drug inlet 20 is a portion into which the drug is sucked when the patient inhales the dry powder drug, and may be formed in a tube shape. In the present embodiment, the drug inlet 20 is formed over the outer housing 12 and the inner housing 14, and a gap G for air entry is formed between the outer housing 12 and the inner housing 14. As the gap G is formed in this way, the suction speed of the dry powder drug sucked through the drug inlet 20 may be increased by the air sucked through the gap G. The gap G is not only formed for the air inflow, but may be used as a space where the lever 4, pulled by the patient, moves for inhalation of the dry powder drug.

Figure 2:
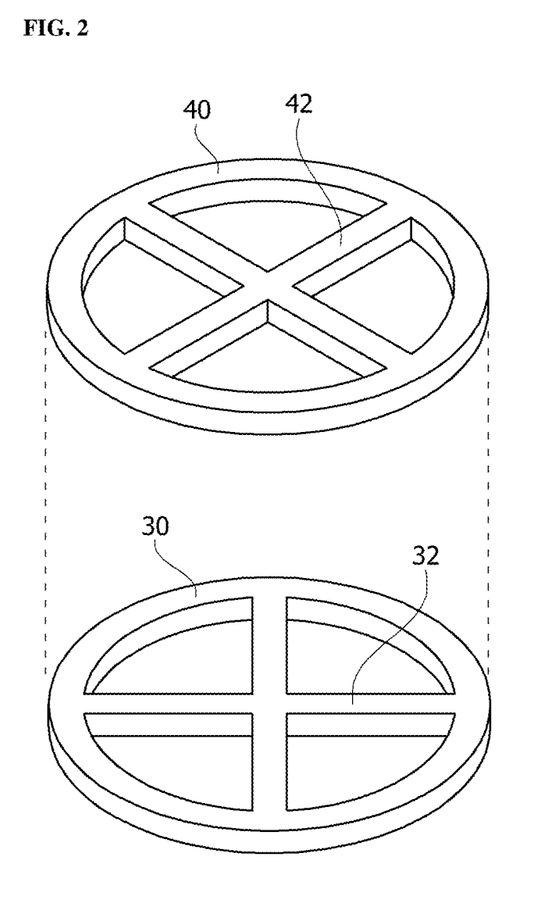
Figure 3:
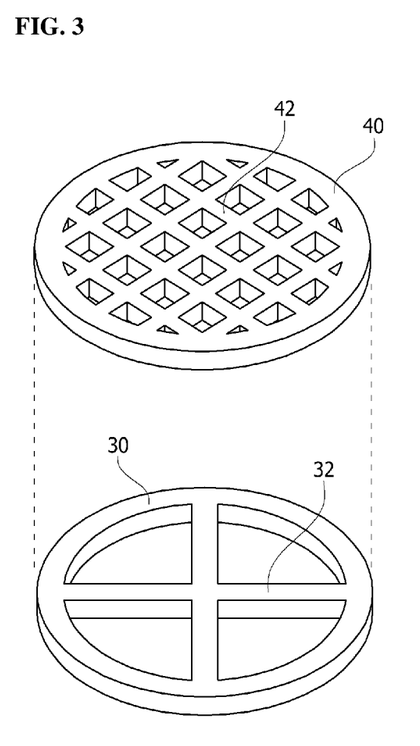

At least two mesh networks 30, 40, and 50 may be installed on the path of the drug inlet 20. The mesh networks 30, 40 and 50 are portions that are provided for collision with the dry powder drug, and two, three, four or more mesh networks may be installed as shown in FIGS. 2 and 3. As will be described below, the point that the mesh parts 32, 42 and 52 are alternately formed with respect to the suction direction of the dry powder drug means that the arrangement directions of the mesh parts 32, 42 and 52 may be alternated, and the holes constituting the adjacent mesh parts 32, 42 and 52 may be different in size and be alternated.

Hereinafter, the first mesh network 30 and the second mesh network 40 will be described with reference to FIGS. 1 and 2. The mesh networks 30 and 40 may include a first mesh network 30 installed at the inlet of the drug inlet 20; and a second mesh network 40 installed at the outlet of the drug inlet 20. In the above description, the first mesh network 30 and the second mesh network 40 have been described as being installed at the entrance and the exit of the drug inlet 20, respectively, but the present invention is not necessarily limited thereto. The first mesh network 30 and the second mesh network 40 only need to be spaced apart from each other on the drug inlet 20.

In the present embodiment, the first mesh network 30 installed at the bottom is a portion that collides with the dry powder drug primarily. The first mesh part 32 formed in the first mesh network 30 is formed to have a suitable density for collision with the dry powder drug. The dry powder drug contained in the drug container 62 may be contained in the drug container 62 for a considerable period depending on the time of use. Then, since the powdered drugs are aggregated, the first mesh part 32 serves to separate the dry powder drugs from each other through collision. Separating the dry powder drugs from each other here means that the powder spreads without clumping.

Next, the second mesh network 40 installed at the top is a portion colliding with the dry powder drug secondarily. The second mesh part 42 formed in the second mesh network 40 is a portion where the dry powder drug having passed through the first mesh network 30 passes before being sucked into the mouth of the patient, and the second mesh part 42 serves to separate the active ingredient and the carrier from the dry powder drug containing the active ingredient and the carrier. The dry powder drug contains an active ingredient that is delivered to the lungs to activate the pharmacological effect and a carrier that moves the active ingredient into the human body. In order to maximize the delivery of the active ingredient to the lungs, it is necessary to apply a second collision to the dry powder drug. Maximum delivery of the active ingredient to the lungs means that the effective amount of the drug is maximized.

As described above, in the present embodiment, the active ingredient and the carrier are separated by applying two or more collisions of the dry powder drug including the active ingredient and the carrier so that the effective ingredient is more effectively delivered to the lungs. Of course, not all dry powder drugs are separated from the carrier through the secondary collision, but the result of the experiment with the inhaler designed in this structure (to be described later) shows that the effective amount of the active ingredient significantly increased.

On the other hand, in the present embodiment, in order to increase the collision force with the dry powder drug, adjacent mesh parts 32 and 42 are alternately formed with respect to the suction direction of the dry powder drug.

Referring to FIG. 2, the first mesh part 32 and the second mesh part 42 are each formed in a cross shape, and the second mesh part 42 is alternately arranged so that the cross shape forms 45° with the first mesh part 32. As shown in FIG. 2, when the shapes of the mesh portions 32 and 42 are alternately formed, the likelihood of the dry powder drug passing through the first mesh part 32 to collide in the second mesh part 42 increases, and therefore the effective amount of the dry powder drug can be increased through the secondary collision.

Referring to FIG. 3, the sizes of the holes constituting the first mesh part 32 and the second mesh part 42 are formed differently. That is, the second mesh part 42 is formed denser than the first mesh part 32. In this case, as shown in FIG. 2, the likelihood of the dry powder drug passing through the first mesh part 32 to collide in the second mesh part 42 increases, so that the effective amount of the dry powder drug can be increased through the second collision.

Figure 4:
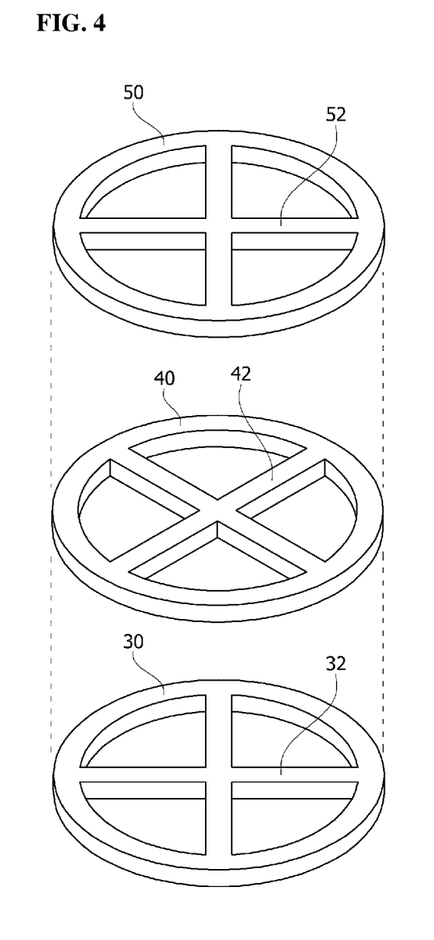

Meanwhile, referring to FIG. 4, three mesh networks 30, 40, and 50 may be arranged in order from the bottom. Here, the mesh networks 30, 40, and 50 are alternately arranged such that the first mesh part 32 and the second mesh part 42 are alternately arranged to have a 45° cross shape, and the second mesh part 42 and the third mesh part 52 are also alternately arranged to have a 45° cross shape. Then, whenever the dry powder drug passes through each mesh network 30, 40 or 50, it is possible to increase the possibility of colliding with the next mesh network 30, 40 or 50.

Here, the mesh network 30, 40 or 50 described above may be formed in a grid form on the mesh part 32, 42 or 52 that is an injection molding, as shown in FIGS. 2 to 4, or may be what is generated by densely forming to have a polygonal hole with a thin iron wire. That is, the mesh networks 30, 40, and 50 need only be formed with holes having various sizes, and the material or shape thereof may be variously formed according to the characteristics of the dry powder drug.

Figure 5:
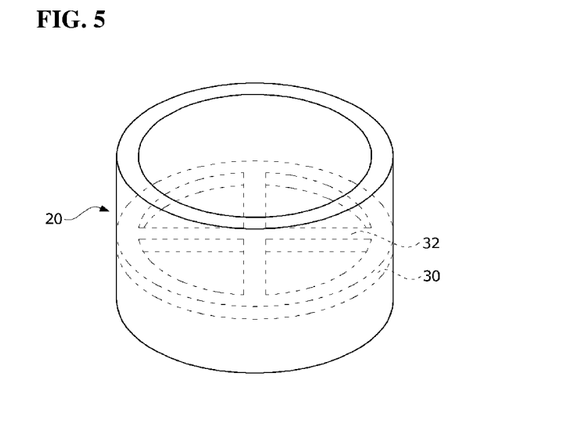

Also, referring to FIG. 5, the first mesh network 30 installed at the lowermost end of the mesh networks 30, 40, and 50 may be disposed at a position spaced upwardly from an inlet of the drug inlet 20. This is to prevent the dry powder drug from falling to the drug container 62 or falling and being attached to the inner housing 14 by increasing the height of the first mesh network 30 where the dry powder drug primarily collides.

Figure 6:
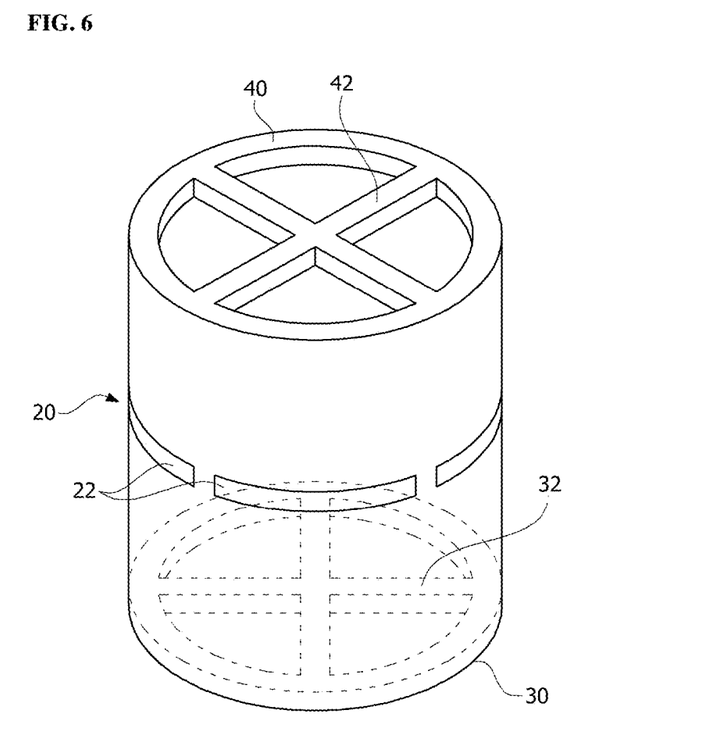

Meanwhile, FIG. 6 is a view showing a drug intake according to another embodiment of the present invention. Referring to FIG. 6, an inlet hole 22 for the air inflow from the outside is formed on the side of the drug inlet (20). The inlet hole 22 may be formed in the form of a slot along the circumferential surface of the drug inlet 20. Although not shown in the figure, the inlet hole 22 may be in the form of a hole formed along the circumferential surface of the drug inlet 20.

It has been mainly described above that at least two mesh networks 30, 40 and 50 are installed. However, only one mesh network 30, 40 or 50 may be installed on the path of the drug inlet 20. In this case, if the hole size (density) of the mesh portions 32, 42, and 52 constituting the mesh networks 30, 40, and 50 are properly configured, the above-described effects can be realized.

The mesh networks 30, 40, and 50 described above may be made of water-soluble materials. This is because the active ingredient constituting the dry powder drug is a water-soluble material and the carrier is a fat-soluble material. That is, if the mesh network 30, 40 or 50 is made of a water-soluble material, the effective ingredient may not be attached to the mesh network 30, 40, 50, but only a collision force may be applied. Alternatively, the water-soluble material may be coated on the surface of the mesh network 30, 40, or 50.

On the other hand, the active ingredient constituting the dry powder drug administered to the dry powder inhaler according to an embodiment of the present invention may be one or more selected from the group consisting of Fluticasone, Salmeterol, Arformoterol, Budesonide, Fenotrol, Procaterol, Levalbuterol, Salbutamol, Albuterol, Terbutaline, Formoterol, Inoteraterol, Olodaterol, Vilanterol, Ipratropium, Oxitropium, Aclidinium, Glycopyrronium, Tiotropium, Umeclidinium, Beclomethasone, Ciclesonide, Triamcinolone, Mometasone, Gefitinib, Erlotinib, Afatinib, Ossimtinib, Olmutinib, Crostinib, Ceritinib, Levodopa, Quinolones and their respective pharmaceutically acceptable salts.

Fluticasone, Salmeterol, Arformoterol, Budesonide, Fenotrol, Procaterol, Levalbuterol, Salbutamol, Albuterol, Terbutaline, Formoterol, Inoteraterol, Olodaterol, Vilanterol, Ipratropium, Oxitropium, Aclidinium, Glycopyrronium, Tiotropium, Umeclidinium, Beclomethasone, Cyclosonide, Triamcinolone, Mometasone, or each salt thereof can be used as a medicine for asthma or COPD.

Gefitinib, Erlotinib, Afatinib, Osimitinib, Olmutinib, Crizotinib, Ceritinib or each salt thereof can be used as a targeted drug therapy for lung cancer.

Levodopa or each salt thereof can be used as a therapeutic agent for Parkinson's disease or degenerative brain disease.

Quinolones or their respective salts can be used as antibiotics.

In addition, the active ingredient constituting the dry powder drug administered to the dry powder inhaler according to an embodiment of the present invention may be one or more selected from the group consisting of variety of hormone drugs, preferably insulin, Glucagon-Like Peptide (GLP), Glucose-dependent Insulinotropic Polypeptide (GIP) Human Growth Hormone (HGH), Parathyroid Hormone (PTH), Erythropoiesis-Stimulating Agents (ESA), and analogs thereof.

The particle size distribution of the active ingredient or the carrier of the dry powder drug may be different, and the particle size to the particle size distribution may be measured by, for example, a laser diffraction method.

The active ingredient constituting the dry powder drug administered to the dry powder inhaler according to an embodiment of the present invention may have a particle size of 0.1 to 10.0 µm.

The carrier constituting the dry powder drug administered to the dry powder inhaler according to an embodiment of the present invention may be one selected from the group consisting of lactose, glucose, fructose, sucrose, maltose, raffinose, melezitose, mannitol, lactitol, maltitol, xylitol, dextrin and starch, but is not limited thereto, and carriers having the features mentioned in the pharmacopeias may generally be applied.

The carrier constituting the dry powder drug administered to the dry powder inhaler according to an embodiment of the present invention may have a particle size of 1 to 200 µm.

On the other hand, dry powder inhaler according to the present invention may be used for treating asthma or COPD; for targeted treatment of lung cancer; for treating Parkinson's disease or degenerative brain disease; as antibiotics; for treating diabetes or obesity; or for treating anemia, and the dry powder inhaler may be a single dose inhaler or a multiple dose inhaler.

EXAMPLES

1. Test Condition

Figure 1:
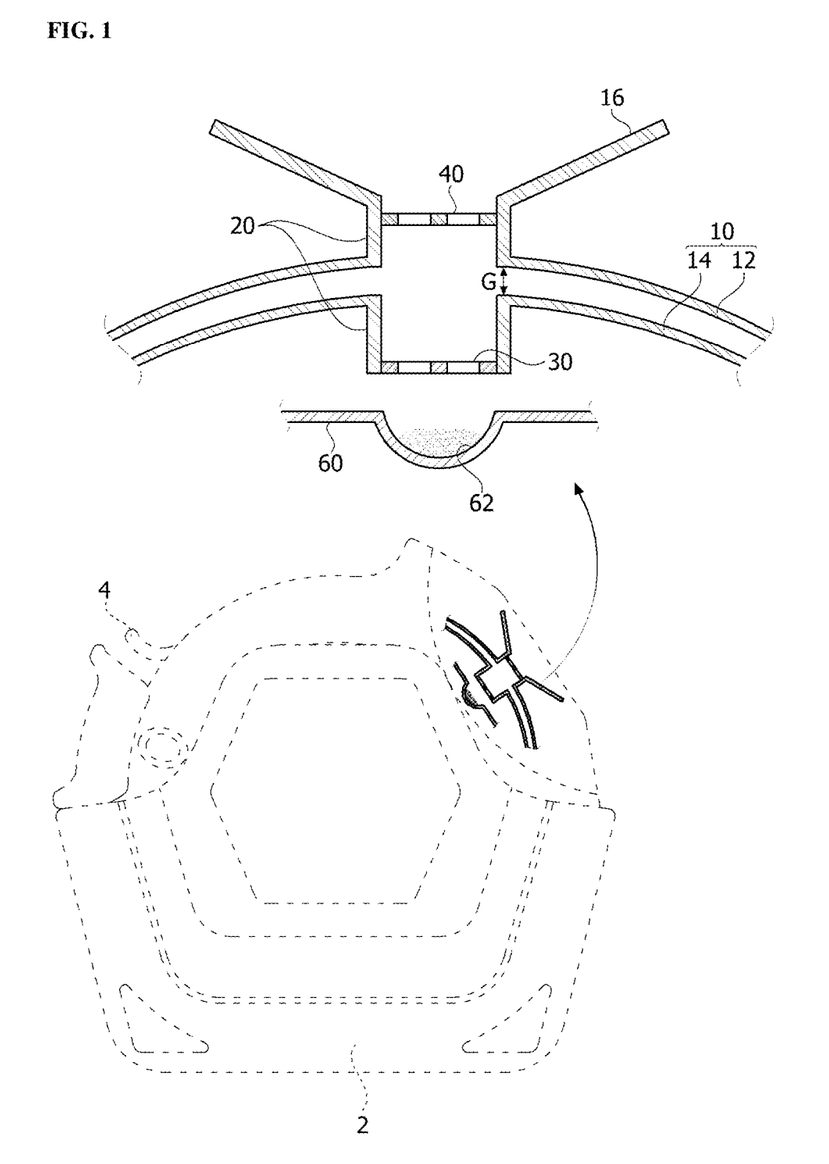

As shown in FIGS. 1 to 3, KUPD #1 and KUPD #2 according to an embodiment of the present invention were produced, respectively.

Here, in KUPD #1, only two mesh networks 30, 40, and 50 were installed as shown in FIGS. 1 and 2, and in KUPD #2, three mesh networks 30, 40, and 50 were installed as shown in FIG. 3.

KUPD #1 and KUPD #2 both contained fluticasone and salmeterol as active ingredients and lactose as a carrier.

Figure 7:
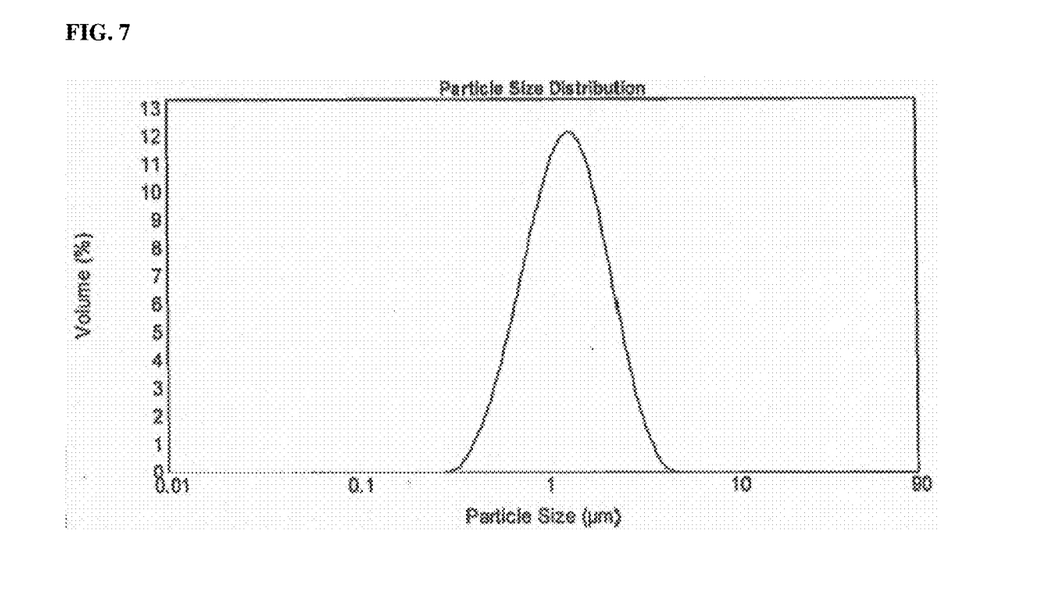

As a result of measuring the particle size of fluticasone used as an active ingredient of a dry powder drug contained in a dry powder inhaler according to an embodiment of the present invention, D (diameter) 10 was measured as 0.7 µM, D 50 was measured as 1.3 µM, and D 90 was measured as 2.3 µM, respectively. Further, the overall particle size distribution was as shown in FIG. 7.

Figure 8:
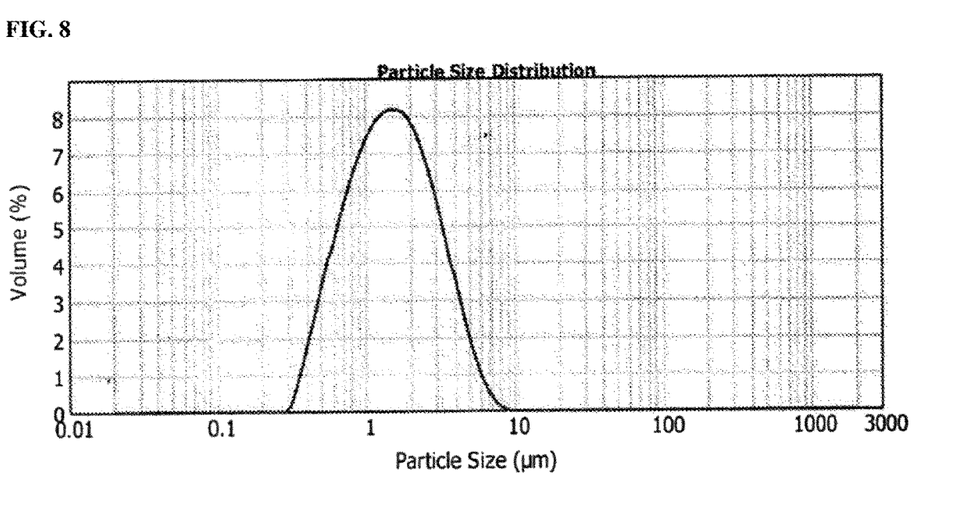

As a result of measuring the particle size of salmeterol used as an active ingredient of a dry powder drug contained in a dry powder inhaler according to an embodiment of the present invention, D 10 was measured as less than 0.7 µm, D 50 was measured as less than 2.1 µm, and D 90 was measured as less than 4.8 µM, respectively. Further, the overall particle size distribution was as shown in FIG. 8.

As a result of measuring the particle size of the lactose used as a carrier of the dry powder drug contained in the dry powder inhaler according to an embodiment of the present invention by using a laser diffraction method, D 10 was measured as 5 to 15 µm, D 50 was measured as 50 to 100 µM, and D 90 was measured as 120 to 175 µM, respectively.

2. Test Method

In order to measure the effective particle amount of the dry powder drug, an artificial trachea and lung model non-clinical test device (Next Generation Pharmaceutical Impactor, NGI) was used. Each stage of the NGI is a device in which each part of the human lung is modeled, and stages 1 to 7 represent pharynx, trachea, bronchi and alveoli, respectively.

Drugs, which can exhibit valid effects when absorbed in the bronchi, such as fluticasone and salmeterol, which are used for respiratory expansion, can exhibit effects only when delivered to and absorbed by the bronchial stage, in which stages 3 to 5 of the NGI correspond to the bronchial stage. Therefore, the amount of NGI delivered to stages 3 to 5 was measured to confirm the amount of effective particles delivered to the bronchi.

As a method for measuring the effective particle amount of the active ingredient delivered to the bronchi using the NGI, the method described in the US Pharmacopoeia (USP), Volume 28, Section <601> was applied. The specific method is as follows.

① A dry powder drug was connected to an induction port with a mouthpiece.
② The dry powder drug was delivered using an air pump (60 L/min).
③ The delivered dry powder drug was collected from the plates of each stage and analyzed to determine the effective particle amount.

3. Comparative Example

Figure 9:
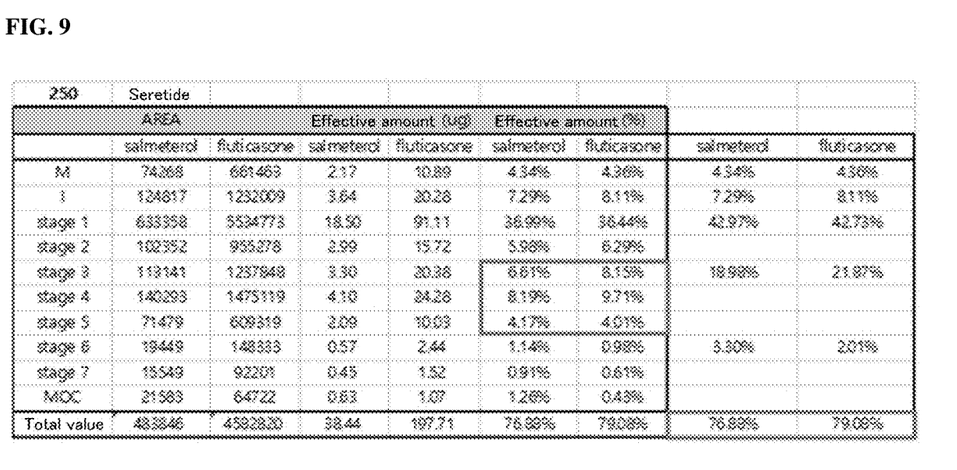

The result of confirming the delivery amount of NGI to each stage according to the above test method using the seretide 250 as a reference drug is shown in FIG. 9.

Salmeterol delivery to stages 3 to 5 by the reference drug was 18.98% and fluticasone delivery was 21.87%. In addition, the total recovery rate of Salmeterol by the reference drug was 76.88%, and the total recovery rate of Fluticasone was 79.08%.

4. Test Example 1

Figure 10:
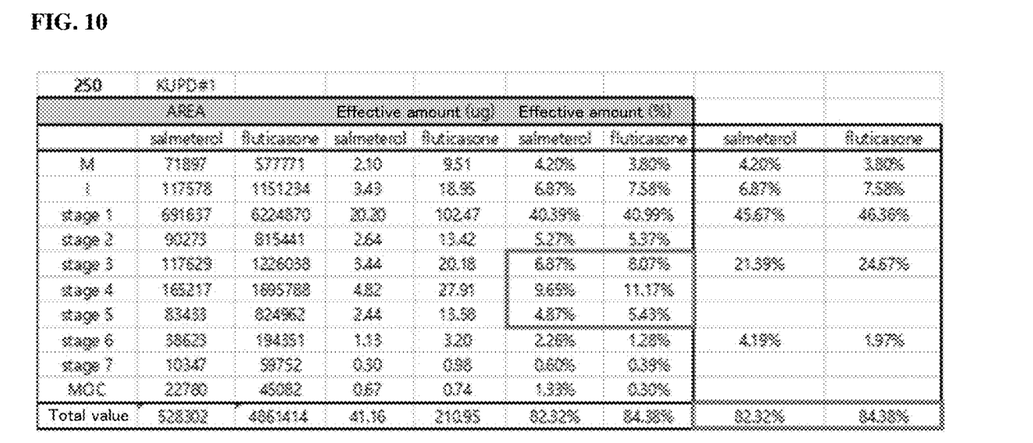

The results of confirming the delivery amount of NGI to each stage according to the above test method using KUPD #1 are shown in FIG. 10.

Salmeterol delivery to stages 3 to 5 by KUPD #1 was 21.39% and Fluticasone delivery was 24.67%. In addition, the total recovery rate of Salmeterol by KUPD #1 was 82.32%, and the total recovery rate of Fluticasone was 84.38%.

As a result of the analysis of Test Example 1, the delivery amount was increased by about 2 to 3% and the overall recovery rate was increased by 5 to 6% compared with the reference drug.

5. Test Example 2

Figure 11:
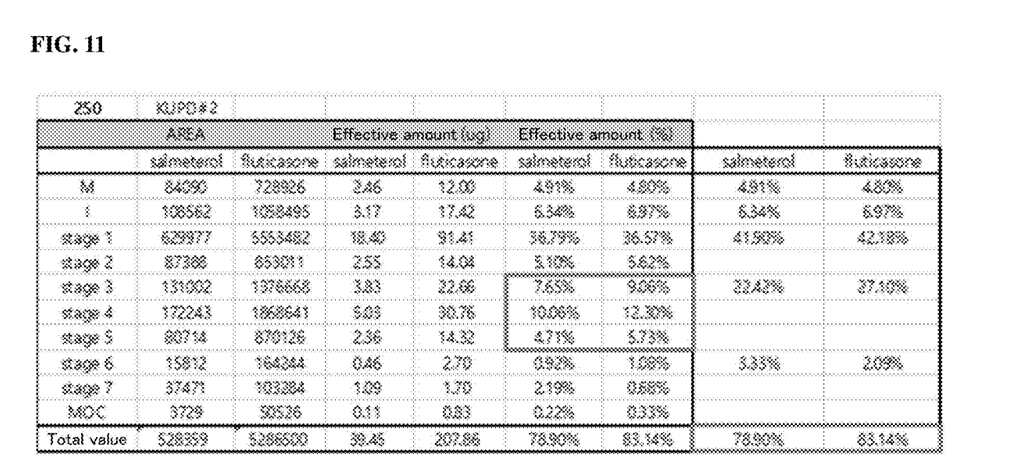

The results of confirming the delivery amount of NGI to each stage according to the above test method using KUPD #2 are shown in FIG. 11.

Salmeterol delivery to stages 3 to 5 by KUPD #2 was 22.42% and Fluticasone delivery was 27.10%. In addition, the total recovery rate of Salmeterol by KUPD #2 was 78.90%, and the total recovery rate of Fluticasone was 83.14%.

As a result of the analysis of Test Example 2, the delivery amount was increased by about 3 to 6% and the overall recovery rate was increased by 2 to 5% compared with the reference drug.

While the foregoing has been described with reference to specific embodiments of the present invention, those skilled in the art will appreciate that various modifications and changes can be made in the present invention without departing from the spirit and scope of the invention as set forth in the claims below.

The invention claimed is:

1. An inhaler for administering a dry powder drug containing an active ingredient and a carrier, the inhaler comprising:
   an inhaler housing;
   a drug container configured to be provided in the inhaler housing and accommodate the dry powder drug;
   a drug inlet disposed above the drug container and through which the dry powder drug is configured to be inhaled; and
   mesh networks installed on a path of the drug inlet and each having a mesh part for collision with the dry powder drug formed therein, the mesh networks comprising a first mesh network and a second mesh network,
   wherein the first mesh network comprises a first circular rim and first spokes extending from a center point within the first circular rim to the first circular rim, and the second mesh network comprises a second circular rim and second spokes extending from a center point within the second circular rim to the second circular rim,
   wherein the first and second spokes are disposed in a manner that the first spokes do not overlap with the second spokes with respect to an inhaling direction of the dry powder drug, and
   wherein the inhaler housing comprises:
      an outer housing comprising the first mesh network; and
      an inner housing comprising the second mesh network, the inner housing accommodated in the outer housing, wherein the drug inlet is formed through the outer housing and the inner housing, and
      a gap for air inflow is formed between the outer housing and inner housing, the gap extending between the first mesh network and the second mesh network, the gap also providing a space for movement of a lever for actuation of the inhaler.

2. The inhaler of claim 1, wherein an inlet hole for the air inflow from an outside is formed at one side of the inhaler housing.

3. The inhaler of claim 1, wherein
   the first mesh network is installed at an entrance of the drug inlet; and
   the second mesh network is installed at an exit of the drug inlet.

4. The inhaler of claim 1, wherein a mesh network installed at a lowest end among the mesh networks is disposed at a position spaced upwardly from an entrance of the drug inlet.

5. The inhaler of claim 1, wherein the density of mesh parts increases from a bottom to a top.

6. The inhaler of claim 1, wherein the mesh networks are made of a water-soluble material.

7. The inhaler of claim 1, wherein a water-soluble material is coated on the surface of the mesh networks.

8. The inhaler of claim 1, wherein the drug container contains the active ingredient and the carrier, and
   wherein the active ingredient is one or more selected from the group consisting of Fluticasone, Salmeterol, Arformoterol, Budesonide, Fenotrol, Procaterol, Levalbuterol, Salbutamol, Albuterol, Terbutaline, Formoterol, Indacaterol, Olodaterol, Vilanterol, Ipratropium, Oxitropium, Aclidinium, Glycopyrronium, Tiotropium, Umeclidinium, Beclomethasone, Ciclesonide, Triamcinolone, Mometasone; Gefitinib, Erlotinib, Afatinib, Ossimtinib, Olmutinib, Crizotinib and Seritinib; Levodopa; Quinolones, and their pharmaceutically acceptable salts.

9. The inhaler of claim 1, wherein the drug container contains the active ingredient and the carrier, and
   wherein the active ingredient is one or more selected from the group consisting of Insulin, Glucagon-Like Peptide (GLP), Glucose-dependent Insulinotropic Polypeptide (GIP), Human Growth Hormone (HGH), Parathyroid Hormone (PTH), Erythropoiesis-Stimulating Agents (ESA) and their analogs.

10. The inhaler of claim 1, wherein the drug container contains the active ingredient and the carrier, and
    wherein the active ingredient has a particle size of 0.1 to 10.0 μm.

11. The inhaler of claim 1, wherein the drug container contains the active ingredient and the carrier, and
    wherein the carrier is one or more selected from the group consisting of lactose, glucose, fructose, sucrose, maltose, raffinose, melezitose, mannitol, lactitol, maltitol, xylitol, dextrin and starch.

12. The inhaler of claim 1, wherein the drug container contains the active ingredient and the carrier, and
    wherein the carrier has a particle size of 1 to 200 μm.

13. The inhaler of claim 1, wherein the center point within the first circular rim and the center point within the second circular rim share an axis in the inhaling direction of the dry powder drug.

* * * * *